(12) United States Patent
Pal et al.

(10) Patent No.: US 7,766,934 B2
(45) Date of Patent: *Aug. 3, 2010

(54) EMBOLIC PROTECTION DEVICE WITH AN INTEGRAL BASKET AND BAG

(75) Inventors: Dharmendra Pal, Wilmington, MA (US); David C. Lentz, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 807 days.

This patent is subject to a terminal disclaimer.

(21) Appl. No.: 11/484,464

(22) Filed: Jul. 11, 2006

(65) Prior Publication Data

US 2007/0016246 A1    Jan. 18, 2007

Related U.S. Application Data

(60) Provisional application No. 60/698,350, filed on Jul. 12, 2005.

(51) Int. Cl.
*A61M 29/00* (2006.01)
(52) U.S. Cl. ..................................... 606/200
(58) Field of Classification Search ................ 606/198, 606/200, 159; 604/104, 105–107
See application file for complete search history.

(56) References Cited

U.S. PATENT DOCUMENTS

| 3,547,103 A | 12/1970 | Cook |
| 3,635,223 A | 1/1972 | Klieman |
| 3,923,065 A | 12/1975 | Nozick et al. |
| 3,952,747 A | 4/1976 | Kimmell, Jr. |
| 3,978,863 A | 9/1976 | Fettel et al. |
| 3,996,938 A | 12/1976 | Clark, III |
| 4,425,908 A | 1/1984 | Simon |
| 4,494,531 A | 1/1985 | Gianturco |
| 4,548,206 A | 10/1985 | Osborne |
| 4,561,439 A | 12/1985 | Bishop et al. |
| 4,619,246 A | 10/1986 | Molgaard-Nielsen et al. |
| 4,643,184 A | 2/1987 | Mobin-Uddin |
| 4,646,736 A | 3/1987 | Auth |
| 4,650,472 A | 3/1987 | Bates |

(Continued)

FOREIGN PATENT DOCUMENTS

WO     WO 96/10591     4/1996

(Continued)

OTHER PUBLICATIONS

Rubicon Embolic Filter, the Next Generation of EM, Rubicon Medical, www.rubiconmed.com, Jun. 28, 2005.

*Primary Examiner*—Michael J Milano
*Assistant Examiner*—Victor X Nguyen
(74) *Attorney, Agent, or Firm*—Brinks Hofer Gilson & Lione (57) ABSTRACT

An embolic protection device includes a basket defined by a section of a set of wires arranged as a plurality of struts. These struts are coupled together at their distal ends as well as to the distal end of a core wire or mandrel. Another section of the wires spirals around the core wire to define a hollow channel in which the core wire can reciprocate. Thus, pulling or pushing a proximal end of the core wire relative to the struts expands or contracts the basket. A filter bag is attached to the basket for capturing clots when the basket is in an expanded configuration.

18 Claims, 3 Drawing Sheets

U.S. PATENT DOCUMENTS

| | | |
|---|---|---|
| 4,665,906 A | 5/1987 | Jervis |
| 4,669,464 A | 6/1987 | Sulepov |
| 4,688,553 A | 8/1987 | Metals |
| 4,723,549 A | 2/1988 | Wholey et al. |
| 4,727,873 A | 3/1988 | Mobin-Uddin |
| 4,817,600 A | 4/1989 | Herms et al. |
| 4,824,435 A | 4/1989 | Giesy et al. |
| 4,832,055 A | 5/1989 | Palestrant |
| 4,873,978 A | 10/1989 | Ginsburg |
| 4,943,297 A | 7/1990 | Saveliev et al. |
| 4,957,501 A | 9/1990 | Lahille et al. |
| 4,990,156 A | 2/1991 | Lefebvre |
| 5,053,008 A | 10/1991 | Bajaj |
| 5,059,205 A | 10/1991 | El-Nounou et al. |
| 5,069,226 A | 12/1991 | Yamauchi et al. |
| 5,100,423 A | 3/1992 | Fearnot |
| 5,108,418 A | 4/1992 | Lefebvre |
| 5,108,419 A | 4/1992 | Reger et al. |
| 5,112,347 A | 5/1992 | Taheri |
| 5,129,890 A | 7/1992 | Bates et al. |
| 5,133,733 A | 7/1992 | Rasmussen et al. |
| 5,147,379 A | 9/1992 | Sabbaghian et al. |
| 5,152,777 A | 10/1992 | Goldberg |
| 5,160,342 A | 11/1992 | Reger |
| 5,234,458 A | 8/1993 | Metais |
| 5,242,462 A | 9/1993 | El-Nounou |
| 5,243,996 A | 9/1993 | Hall |
| 5,251,640 A | 10/1993 | Osborne |
| 5,263,964 A | 11/1993 | Purdy |
| 5,300,086 A | 4/1994 | Gory et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,417,708 A | 5/1995 | Hall et al. |
| 5,527,338 A | 6/1996 | Purdy |
| 5,531,788 A | 7/1996 | Dibie et al. |
| 5,549,626 A | 8/1996 | Miller et al. |
| 5,562,698 A | 10/1996 | Parker |
| 5,601,595 A | 2/1997 | Smith |
| 5,624,461 A | 4/1997 | Mariant |
| 5,626,605 A | 5/1997 | Irie et al. |
| 5,634,942 A | 6/1997 | Chevillon et al. |
| 5,649,953 A | 7/1997 | Lefebvre |
| 5,669,933 A | 9/1997 | Simon et al. |
| 5,681,347 A | 10/1997 | Cathcart et al. |
| 5,690,667 A | 11/1997 | Gia |
| 5,693,067 A | 12/1997 | Purdy |
| 5,695,518 A | 12/1997 | Laerum |
| 5,695,519 A | 12/1997 | Summers et al. |
| 5,709,704 A | 1/1998 | Nott et al. |
| 5,713,853 A | 2/1998 | Clark et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,769,871 A | 6/1998 | Mers et al. |
| 5,795,322 A | 8/1998 | Boudewijn |
| 5,800,457 A | 9/1998 | Gelbfish et al. |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,830,230 A | 11/1998 | Berryman et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,876,367 A | 3/1999 | Kaganov et al. |
| 5,893,869 A | 4/1999 | Barnhart et al. |
| 5,895,391 A | 4/1999 | Farnholtz |
| 5,895,399 A | 4/1999 | Barbut et al. |
| 5,895,410 A | 4/1999 | Forber et al. |
| 5,908,435 A | 6/1999 | Samuels |
| 5,910,154 A | 6/1999 | Tsugita et al. |
| 5,911,704 A | 6/1999 | Humes |
| 5,911,717 A | 6/1999 | Jacobsen et al. |
| 5,911,734 A | 6/1999 | Tsugita et al. |
| 5,919,224 A | 7/1999 | Thompson et al. |
| 5,925,062 A | 7/1999 | Purdy |
| 5,925,063 A | 7/1999 | Khosravi |
| 5,928,260 A | 7/1999 | Chine et al. |
| 5,928,261 A | 7/1999 | Ruiz |
| 5,938,683 A | 8/1999 | Lefebvre |
| 5,941,896 A | 8/1999 | Kerr |
| 5,944,728 A | 8/1999 | Bates |
| 5,947,985 A | 9/1999 | Imran |
| 5,947,995 A | 9/1999 | Samuels |
| 5,948,017 A | 9/1999 | Taheri |
| 5,951,567 A | 9/1999 | Javier, Jr. et al. |
| 5,954,741 A | 9/1999 | Fox |
| 5,954,742 A | 9/1999 | Osypka |
| 5,954,745 A | 9/1999 | Gertler et al. |
| 5,968,057 A | 10/1999 | Taheri |
| 5,968,071 A | 10/1999 | Chevillon et al. |
| 5,972,019 A | 10/1999 | Engelson et al. |
| 5,976,162 A | 11/1999 | Doan et al. |
| 5,976,172 A | 11/1999 | Homsma et al. |
| 5,980,555 A | 11/1999 | Barbut et al. |
| 5,984,947 A | 11/1999 | Smith |
| 5,989,281 A | 11/1999 | Barbut et al. |
| 6,001,118 A | 12/1999 | Daniel et al. |
| 6,007,557 A | 12/1999 | Ambrisco et al. |
| 6,007,558 A | 12/1999 | Ravenscloth et al. |
| 6,010,522 A | 1/2000 | Barbut et al. |
| 6,013,093 A | 1/2000 | Nott et al. |
| 6,015,424 A | 1/2000 | Rosenbluth et al. |
| 6,027,520 A | 2/2000 | Tsugita et al. |
| 6,036,717 A | 3/2000 | Mers Kelly et al. |
| 6,036,720 A | 3/2000 | Abrams et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,745 A | 5/2000 | Gelbfish |
| 6,059,814 A | 5/2000 | Ladd |
| 6,063,113 A | 5/2000 | Kavteladze et al. |
| 6,066,158 A | 5/2000 | Engelson et al. |
| 6,068,645 A | 5/2000 | Tu |
| 6,074,357 A | 6/2000 | Kaganov et al. |
| 6,077,274 A | 6/2000 | Ouchi et al. |
| 6,080,178 A | 6/2000 | Meglin |
| 6,083,239 A | 7/2000 | Addis |
| 6,086,577 A | 7/2000 | Ken et al. |
| 6,086,605 A | 7/2000 | Barbut et al. |
| 6,093,199 A | 7/2000 | Brown et al. |
| 6,096,053 A | 8/2000 | Bates |
| 6,099,549 A | 8/2000 | Bosma et al. |
| 6,106,497 A | 8/2000 | Wang |
| 6,126,672 A | 10/2000 | Berryman et al. |
| 6,126,673 A | 10/2000 | Kim et al. |
| 6,129,739 A | 10/2000 | Khosravi |
| 6,136,016 A | 10/2000 | Barbut et al. |
| 6,146,396 A | 11/2000 | Konya et al. |
| 6,146,404 A | 11/2000 | Kim et al. |
| 6,152,931 A | 11/2000 | Nadal et al. |
| 6,152,946 A | 11/2000 | Broome et al. |
| 6,152,947 A | 11/2000 | Ambrisco et al. |

| | | | | | | |
|---|---|---|---|---|---|---|
| 6,156,061 | A | 12/2000 | Wallace et al. | 6,361,546 B1 | 3/2002 | Khosravi |
| 6,159,230 | A | 12/2000 | Samuels | 6,361,547 B1 | 3/2002 | Hieshima |
| 6,165,179 | A | 12/2000 | Cathcart et al. | 6,364,895 B1 | 4/2002 | Greenhalgh |
| 6,165,198 | A | 12/2000 | McGurk et al. | 6,364,896 B1 | 4/2002 | Addis |
| 6,165,199 | A | 12/2000 | Barbut | 6,368,338 B1 | 4/2002 | Konya et al. |
| 6,165,200 | A * | 12/2000 | Tsugita et al. .............. 606/200 | 6,371,969 B1 | 4/2002 | Tsugita et al. |
| 6,168,579 | B1 | 1/2001 | Tsugita et al. | 6,371,970 B1 | 4/2002 | Khosravi et al. |
| 6,168,603 | B1 | 1/2001 | Leslie et al. | 6,371,971 B1 | 4/2002 | Tsugita et al. |
| 6,168,622 | B1 | 1/2001 | Mazzocchi | 6,375,670 B1 | 4/2002 | Greenhalgh |
| 6,171,327 | B1 | 1/2001 | Daniel et al. | 6,379,374 B1 | 4/2002 | Hieshima et al. |
| 6,171,328 | B1 | 1/2001 | Addis | 6,383,146 B1 | 5/2002 | Klint |
| 6,174,318 | B1 | 1/2001 | Bates et al. | 6,383,174 B1 | 5/2002 | Eder |
| 6,179,851 | B1 | 1/2001 | Barbut et al. | 6,383,193 B1 | 5/2002 | Cathcart et al. |
| 6,179,859 | B1 | 1/2001 | Bates et al. | 6,383,196 B1 | 5/2002 | Leslie et al. |
| 6,179,860 | B1 | 1/2001 | Fulton, III et al. | 6,383,205 B1 | 5/2002 | Samson et al. |
| 6,179,861 | B1 | 1/2001 | Khosravi et al. | 6,383,206 B1 | 5/2002 | Gillick et al. |
| 6,187,025 | B1 | 2/2001 | Machek | 6,391,044 B1 | 5/2002 | Yadav et al. |
| 6,193,739 | B1 | 2/2001 | Chevillon et al. | 6,391,045 B1 | 5/2002 | Kim et al. |
| 6,203,561 | B1 | 3/2001 | Ramee et al. | 6,395,014 B1 | 5/2002 | Macoviak et al. |
| 6,214,025 | B1 | 4/2001 | Thistle et al. | 6,402,771 B1 | 6/2002 | Palmer et al. |
| 6,214,026 | B1 | 4/2001 | Lepak et al. | 6,402,772 B1 | 6/2002 | Amplatz et al. |
| 6,221,091 | B1 | 4/2001 | Khosravi | 6,409,742 B1 | 6/2002 | Fulton, III et al. |
| 6,224,620 | B1 | 5/2001 | Maahs | 6,413,235 B1 | 7/2002 | Parodi |
| 6,231,588 | B1 | 5/2001 | Zadno-Azizi | 6,416,530 B2 | 7/2002 | DeVries et al. |
| 6,231,589 | B1 | 5/2001 | Wessman et al. | 6,419,686 B1 | 7/2002 | McLeod et al. |
| 6,235,044 | B1 | 5/2001 | Root et al. | 6,423,086 B1 | 7/2002 | Barbut et al. |
| 6,235,045 | B1 | 5/2001 | Barbut et al. | 6,425,909 B1 | 7/2002 | Dieck et al. |
| 6,238,412 | B1 | 5/2001 | Dubrul et al. | 6,428,557 B1 | 8/2002 | Hilaire |
| 6,241,746 | B1 | 6/2001 | Bosma et al. | 6,428,558 B1 | 8/2002 | Jones et al. |
| 6,245,087 | B1 | 6/2001 | Addis | 6,428,559 B1 | 8/2002 | Johnson |
| 6,245,088 | B1 | 6/2001 | Lowery | 6,432,122 B1 | 8/2002 | Gilson et al. |
| 6,245,089 | B1 | 6/2001 | Daniel et al. | 6,436,112 B2 | 8/2002 | Wensel et al. |
| 6,251,122 | B1 | 6/2001 | Tsukernik | 6,436,120 B1 | 8/2002 | Meglin |
| 6,254,550 | B1 | 7/2001 | McNamara et al. | 6,436,121 B1 | 8/2002 | Blom |
| 6,254,633 | B1 | 7/2001 | Pinchuk et al. | 6,443,926 B1 | 9/2002 | Kletschka |
| 6,258,026 | B1 | 7/2001 | Ravenscroft et al. | 6,443,971 B1 | 9/2002 | Boylan et al. |
| 6,258,115 | B1 | 7/2001 | Dubrul | 6,443,972 B1 | 9/2002 | Bosma et al. |
| 6,258,120 | B1 | 7/2001 | McKenzie et al. | 6,447,530 B1 | 9/2002 | Ostrovsky et al. |
| 6,261,305 | B1 | 7/2001 | Marotta et al. | 6,447,531 B1 | 9/2002 | Amplatz |
| 6,264,672 | B1 | 7/2001 | Fisher | 6,454,775 B1 * | 9/2002 | Demarais et al. ............ 606/128 |
| 6,267,776 | B1 | 7/2001 | O'Connell | 6,458,139 B1 | 10/2002 | Palmer et al. |
| 6,267,777 | B1 | 7/2001 | Bosma et al. | 6,458,145 B1 | 10/2002 | Ravenscroft et al. |
| 6,273,900 | B1 | 8/2001 | Nott et al. | 6,461,370 B1 | 10/2002 | Gray et al. |
| 6,273,901 | B1 | 8/2001 | Whitcher et al. | 6,468,290 B1 | 10/2002 | Weldon et al. |
| 6,277,125 | B1 | 8/2001 | Barry et al. | 6,468,291 B2 | 10/2002 | Bates et al. |
| 6,277,126 | B1 | 8/2001 | Barry et al. | 6,482,222 B1 | 11/2002 | Bruckheimer et al. |
| 6,277,138 | B1 | 8/2001 | Levinson et al. | 6,485,456 B1 | 11/2002 | Kletschka |
| 6,277,139 | B1 | 8/2001 | Levinson et al. | 6,485,500 B1 | 11/2002 | Kokish et al. |
| 6,280,451 | B1 | 8/2001 | Bates et al. | 6,485,501 B1 | 11/2002 | Green |
| 6,287,321 | B1 | 9/2001 | Jang | 6,485,502 B2 | 11/2002 | Don Michael et al. |
| 6,290,710 | B1 | 9/2001 | Cryer et al. | 6,491,712 B1 | 12/2002 | O'Connor |
| 6,306,163 | B1 | 10/2001 | Fitz | 6,494,895 B2 | 12/2002 | Addis |
| 6,309,399 | B1 | 10/2001 | Barbut et al. | 6,497,709 B1 | 12/2002 | Heath |
| 6,312,444 | B1 | 11/2001 | Barbut | 6,499,487 B1 | 12/2002 | McKenzie et al. |
| 6,319,268 | B1 | 11/2001 | Ambrisco et al. | 6,500,166 B1 | 12/2002 | Zadno Azizi et al. |
| 6,325,815 | B1 | 12/2001 | Kusleika et al. | 6,500,191 B2 | 12/2002 | Addis |
| 6,325,816 | B1 | 12/2001 | Fulton, III et al. | 6,502,606 B2 | 1/2003 | Klint |
| 6,328,755 | B1 | 12/2001 | Marshall | 6,506,203 B1 | 1/2003 | Boyle et al. |
| 6,331,183 | B1 | 12/2001 | Suon | 6,506,205 B2 | 1/2003 | Goldberg et al. |
| 6,331,184 | B1 | 12/2001 | Abrams | 6,508,826 B2 | 1/2003 | Murphy et al. |
| 6,334,864 | B1 | 1/2002 | Amplatz et al. | 6,511,492 B1 | 1/2003 | Rosenbluth et al. |
| 6,336,934 | B1 | 1/2002 | Gilson et al. | 6,511,496 B1 | 1/2003 | Huter et al. |
| 6,340,364 | B2 | 1/2002 | Kanesaka | 6,511,497 B1 | 1/2003 | Braun et al. |
| 6,342,062 | B1 | 1/2002 | Suon et al. | 6,511,503 B1 | 1/2003 | Burkett et al. |
| 6,342,063 | B1 | 1/2002 | DeVries et al. | 6,514,273 B1 | 2/2003 | Voss et al. |
| 6,344,048 | B1 | 2/2002 | Chin et al. | 6,517,559 B1 | 2/2003 | O'Connell |
| 6,344,049 | B1 | 2/2002 | Levinson et al. | 6,520,978 B1 | 2/2003 | Blackledge et al. |
| 6,346,116 | B1 | 2/2002 | Brooks et al. | 6,527,746 B1 | 3/2003 | Oslund et al. |
| 6,348,041 | B1 | 2/2002 | Klint | 6,527,791 B2 | 3/2003 | Fisher |
| 6,348,063 | B1 | 2/2002 | Yassour et al. | 6,527,962 B1 | 3/2003 | Nadal |
| 6,355,051 | B1 | 3/2002 | Sisskind et al. | 6,530,935 B2 | 3/2003 | Wensel et al. |
| 6,358,228 | B1 | 3/2002 | Tubman et al. | 6,530,939 B1 | 3/2003 | Hopkins et al. |
| 6,361,545 | B1 | 3/2002 | Macoviak et al. | 6,530,940 B2 | 3/2003 | Fisher |

| | | | | | | |
|---|---|---|---|---|---|---|
| 6,533,800 B1 | 3/2003 | Barbut | 6,656,201 B2 | 12/2003 | Ferrera et al. | |
| 6,537,293 B1 | 3/2003 | Berryman et al. | 6,656,202 B2 | 12/2003 | Papp et al. | |
| 6,537,294 B1 | 3/2003 | Boyle et al. | 6,656,203 B2 | 12/2003 | Roth et al. | |
| 6,537,296 B2 | 3/2003 | Levinson et al. | 6,656,204 B2 | 12/2003 | Ambrisco et al. | |
| 6,537,297 B2 | 3/2003 | Tsugita et al. | 6,656,351 B2 | 12/2003 | Boyle | |
| 6,540,722 B1 | 4/2003 | Boyle et al. | 6,660,021 B1 | 12/2003 | Palmer et al. | |
| 6,540,767 B1 | 4/2003 | Walak et al. | 6,663,613 B1 | 12/2003 | Evans et al. | |
| 6,540,768 B1 | 4/2003 | Diaz et al. | 6,663,650 B2 | 12/2003 | Sepetka et al. | |
| 6,544,221 B1 | 4/2003 | Kokish et al. | 6,663,651 B2 | 12/2003 | Krolik et al. | |
| 6,544,276 B1 | 4/2003 | Azizi | 6,663,652 B2 | 12/2003 | Daniel et al. | |
| 6,544,279 B1 | 4/2003 | Hopkins et al. | 6,695,865 B2 | 2/2004 | Boyle et al. | |
| 6,544,280 B1 | 4/2003 | Daniel et al. | 6,702,834 B1 * | 3/2004 | Boylan et al. | 606/200 |
| 6,547,759 B1 | 4/2003 | Fisher | 6,712,835 B2 | 3/2004 | Mazzocchi et al. | |
| 6,551,303 B1 | 4/2003 | Van Tassel et al. | 6,726,701 B2 | 4/2004 | Gilson et al. | |
| 6,551,341 B2 | 4/2003 | Boylan et al. | 6,758,855 B2 | 7/2004 | Fulton, III et al. | |
| 6,551,342 B1 | 4/2003 | Shen et al. | 6,761,727 B1 | 7/2004 | Ladd | |
| 6,554,849 B1 | 4/2003 | Jones et al. | 6,780,175 B1 | 8/2004 | Sachdeva et al. | |
| 6,558,404 B2 | 5/2003 | Tsukernik | 6,793,668 B1 | 9/2004 | Fisher | |
| 6,558,405 B1 | 5/2003 | McInnes | 6,866,677 B2 | 3/2005 | Douk et al. | |
| 6,558,406 B2 | 5/2003 | Okada | 2001/0000799 A1 | 5/2001 | Wessman et al. | |
| 6,562,058 B2 | 5/2003 | Seguin et al. | 2001/0001817 A1 | 5/2001 | Humes | |
| 6,565,591 B2 | 5/2003 | Brady et al. | 2001/0005789 A1 | 6/2001 | Root et al. | |
| 6,569,147 B1 | 5/2003 | Evans et al. | 2001/0007947 A1 | 7/2001 | Kanesaka | |
| 6,569,183 B1 | 5/2003 | Kim et al. | 2001/0011181 A1 | 8/2001 | DiMatteo | |
| 6,569,184 B2 | 5/2003 | Huter | 2001/0011182 A1 | 8/2001 | Dubrul et al. | |
| 6,575,995 B1 | 6/2003 | Huter et al. | 2001/0012951 A1 | 8/2001 | Bates et al. | |
| 6,575,996 B1 | 6/2003 | Denison et al. | 2001/0016755 A1 | 8/2001 | Addis | |
| 6,575,997 B1 | 6/2003 | Palmer et al. | 2001/0020175 A1 | 9/2001 | Yassour et al. | |
| 6,579,303 B2 | 6/2003 | Amplatz | 2001/0023358 A1 | 9/2001 | Tsukernik | |
| 6,582,396 B1 | 6/2003 | Parodi | 2001/0025187 A1 | 9/2001 | Okada | |
| 6,582,447 B1 | 6/2003 | Patel et al. | 2001/0031980 A1 | 10/2001 | Wensel et al. | |
| 6,582,448 B1 | 6/2003 | Boyle et al. | 2001/0031981 A1 | 10/2001 | Evans et al. | |
| 6,589,230 B2 | 7/2003 | Gia et al. | 2001/0031982 A1 | 10/2001 | Peterson et al. | |
| 6,589,263 B1 | 7/2003 | Hopkins et al. | 2001/0039431 A1 | 11/2001 | DeVries et al. | |
| 6,589,264 B1 | 7/2003 | Barbut et al. | 2001/0039432 A1 | 11/2001 | Whitcher et al. | |
| 6,589,265 B1 | 7/2003 | Palmer et al. | 2001/0041908 A1 | 11/2001 | Levinson et al. | |
| 6,589,266 B2 | 7/2003 | Whitcher et al. | 2001/0041909 A1 | 11/2001 | Tsugita et al. | |
| 6,592,546 B1 | 7/2003 | Barbut et al. | 2001/0044632 A1 | 11/2001 | Daniel et al. | |
| 6,592,606 B2 | 7/2003 | Huter et al. | 2001/0044634 A1 | 11/2001 | Don Michael et al. | |
| 6,596,011 B2 | 7/2003 | Johnson et al. | 2001/0053921 A1 | 12/2001 | Jang | |
| 6,599,307 B1 | 7/2003 | Huter et al. | 2002/0002384 A1 | 1/2002 | Gilson et al. | |
| 6,599,308 B2 | 7/2003 | Amplatz | 2002/0004667 A1 | 1/2002 | Adams et al. | |
| 6,602,271 B2 | 8/2003 | Adams et al. | 2002/0016564 A1 | 2/2002 | Courtney et al. | |
| 6,602,273 B2 | 8/2003 | Marshall | 2002/0016609 A1 | 2/2002 | Wensel et al. | |
| 6,605,102 B1 | 8/2003 | Mazzocchi et al. | 2002/0022858 A1 | 2/2002 | Demond et al. | |
| 6,607,506 B2 | 8/2003 | Kletschka | 2002/0022859 A1 | 2/2002 | Hogendijk | |
| 6,610,077 B1 | 8/2003 | Hancock et al. | 2002/0026211 A1 | 2/2002 | Khosravi et al. | |
| 6,613,074 B1 | 9/2003 | Mitelberg et al. | 2002/0026212 A1 | 2/2002 | Wholey et al. | |
| 6,616,679 B1 | 9/2003 | Khosravi et al. | 2002/0026213 A1 | 2/2002 | Gilson et al. | |
| 6,616,680 B1 | 9/2003 | Thielen | 2002/0032460 A1 | 3/2002 | Kusleika et al. | |
| 6,616,681 B1 | 9/2003 | Hanson et al. | 2002/0032461 A1 | 3/2002 | Marshall | |
| 6,616,682 B2 | 9/2003 | Joergensen et al. | 2002/0042626 A1 | 4/2002 | Hanson et al. | |
| 6,620,148 B1 | 9/2003 | Tsugita | 2002/0042627 A1 | 4/2002 | Brady et al. | |
| 6,620,182 B1 | 9/2003 | Khosravi et al. | 2002/0045915 A1 | 4/2002 | Balceta et al. | |
| 6,623,450 B1 | 9/2003 | Dutta | 2002/0045916 A1 | 4/2002 | Gray et al. | |
| 6,623,506 B2 | 9/2003 | McGuckin, Jr. et al. | 2002/0045918 A1 | 4/2002 | Suon et al. | |
| 6,629,953 B1 | 10/2003 | Boyd | 2002/0049452 A1 | 4/2002 | Kurz et al. | |
| 6,635,068 B1 | 10/2003 | Dubrul et al. | 2002/0049468 A1 | 4/2002 | Streeter et al. | |
| 6,635,069 B1 | 10/2003 | Teoh et al. | 2002/0052627 A1 | 5/2002 | Boylan et al. | |
| 6,635,070 B2 | 10/2003 | Leeflang et al. | 2002/0058904 A1 | 5/2002 | Boock et al. | |
| 6,638,293 B1 | 10/2003 | Makower et al. | 2002/0058911 A1 | 5/2002 | Gilson et al. | |
| 6,638,294 B1 | 10/2003 | Palmer | 2002/0058963 A1 | 5/2002 | Vale et al. | |
| 6,638,372 B1 | 10/2003 | Abrams et al. | 2002/0058964 A1 | 5/2002 | Addis | |
| 6,641,590 B1 | 11/2003 | Palmer et al. | 2002/0062133 A1 | 5/2002 | Gilson et al. | |
| 6,641,605 B1 | 11/2003 | Stergiopulos | 2002/0062134 A1 | 5/2002 | Barbut et al. | |
| 6,645,220 B1 | 11/2003 | Huter et al. | 2002/0062135 A1 | 5/2002 | Mazzocchi et al. | |
| 6,645,221 B1 | 11/2003 | Richter | 2002/0065507 A1 | 5/2002 | Zadno-Azizi | |
| 6,645,222 B1 | 11/2003 | Parodi et al. | 2002/0068954 A1 | 6/2002 | Foster | |
| 6,645,223 B2 | 11/2003 | Boyle et al. | 2002/0068955 A1 | 6/2002 | Khosravi | |
| 6,645,224 B2 | 11/2003 | Gilson et al. | 2002/0072764 A1 | 6/2002 | Sepetka et al. | |
| 6,652,554 B1 | 11/2003 | Wholey et al. | 2002/0072765 A1 | 6/2002 | Mazzocchi et al. | |
| 6,652,557 B1 | 11/2003 | MacDonald | 2002/0077596 A1 | 6/2002 | McKenzie et al. | |
| 6,652,558 B2 | 11/2003 | Patel et al. | 2002/0082558 A1 | 6/2002 | Samson et al. | |

| | | | | | |
|---|---|---|---|---|---|
| 2002/0082639 A1 | 6/2002 | Broome et al. | 2003/0009146 A1 | 1/2003 | Muni et al. |
| 2002/0087187 A1 | 7/2002 | Mazzocchi et al. | 2003/0009189 A1 | 1/2003 | Gilson et al. |
| 2002/0090389 A1 | 7/2002 | Humes et al. | 2003/0009190 A1 | 1/2003 | Kletschka et al. |
| 2002/0091407 A1 | 7/2002 | Zadno-Azizi et al. | 2003/0009191 A1 | 1/2003 | Wensel et al. |
| 2002/0091408 A1 | 7/2002 | Sutton et al. | 2003/0014072 A1 | 1/2003 | Wensel et al. |
| 2002/0091409 A1 | 7/2002 | Sutton et al. | 2003/0018354 A1 | 1/2003 | Roth et al. |
| 2002/0095170 A1 | 7/2002 | Krolik et al. | 2003/0018355 A1 | 1/2003 | Goto et al. |
| 2002/0095171 A1 | 7/2002 | Belef | 2003/0023263 A1 | 1/2003 | Krolik et al. |
| 2002/0095172 A1 | 7/2002 | Mazzocchi et al. | 2003/0023264 A1 | 1/2003 | Dieck et al. |
| 2002/0095173 A1 | 7/2002 | Mazzocchi et al. | 2003/0023265 A1 | 1/2003 | Forber |
| 2002/0095174 A1 | 7/2002 | Tsugita et al. | 2003/0032976 A1 | 2/2003 | Boucck |
| 2002/0099407 A1 | 7/2002 | Becker et al. | 2003/0032977 A1 | 2/2003 | Brady |
| 2002/0103501 A1 | 8/2002 | Diaz et al. | 2003/0040772 A1 | 2/2003 | Hyodoh et al. |
| 2002/0107541 A1 | 8/2002 | Vale et al. | 2003/0045897 A1 | 3/2003 | Huter et al. |
| 2002/0111647 A1 | 8/2002 | Khairkhahan et al. | 2003/0045898 A1 | 3/2003 | Harrison et al. |
| 2002/0111648 A1 | 8/2002 | Kusleika et al. | 2003/0050662 A1 | 3/2003 | Don Michael |
| 2002/0111649 A1 | 8/2002 | Russo et al. | 2003/0055452 A1 | 3/2003 | Joergensen et al. |
| 2002/0116024 A1 | 8/2002 | Goldberg et al. | 2003/0055480 A1 | 3/2003 | Fischell et al. |
| 2002/0120226 A1 | 8/2002 | Beck | 2003/0060843 A1 | 3/2003 | Boucher |
| 2002/0120286 A1 | 8/2002 | DoBrava et al. | 2003/0060844 A1 | 3/2003 | Borillo et al. |
| 2002/0120287 A1 | 8/2002 | Huter | 2003/0065354 A1 | 4/2003 | Boyle et al. |
| 2002/0123720 A1 | 9/2002 | Kusleika et al. | 2003/0065355 A1 | 4/2003 | Weber |
| 2002/0123755 A1 | 9/2002 | Lowe et al. | 2003/0065356 A1 | 4/2003 | Tsugita et al. |
| 2002/0123759 A1 | 9/2002 | Amplatz | 2003/0069596 A1 | 4/2003 | Eskuri |
| 2002/0123766 A1 | 9/2002 | Seguin et al. | 2003/0073979 A1 | 4/2003 | Naimark et al. |
| 2002/0128679 A1 | 9/2002 | Turovskiy et al. | 2003/0074019 A1 | 4/2003 | Gray et al. |
| 2002/0128680 A1 | 9/2002 | Pavlovic | 2003/0078614 A1 | 4/2003 | Salahieh et al. |
| 2002/0128681 A1 | 9/2002 | Broome et al. | 2003/0083692 A1 | 5/2003 | Vrba et al. |
| 2002/0133191 A1 | 9/2002 | Khosravi et al. | 2003/0083693 A1 | 5/2003 | Daniel et al. |
| 2002/0133192 A1 | 9/2002 | Kusleika et al. | 2003/0088211 A1 | 5/2003 | Anderson et al. |
| 2002/0138094 A1 | 9/2002 | Borillo et al. | 2003/0088266 A1 | 5/2003 | Bowlin |
| 2002/0138095 A1 | 9/2002 | Mazzocchi et al. | 2003/0093110 A1 | 5/2003 | Vale |
| 2002/0138096 A1 | 9/2002 | Hieshima | 2003/0093112 A1 | 5/2003 | Addis |
| 2002/0138097 A1 | 9/2002 | Ostrovsky et al. | 2003/0097094 A1 | 5/2003 | Ouriel et al. |
| 2002/0143360 A1 | 10/2002 | Douk et al. | 2003/0097145 A1 | 5/2003 | Goldberg et al. |
| 2002/0143361 A1 | 10/2002 | Douk et al. | 2003/0100917 A1 | 5/2003 | Boyle et al. |
| 2002/0143362 A1 | 10/2002 | Macoviak et al. | 2003/0100918 A1 | 5/2003 | Duane |
| 2002/0151927 A1 | 10/2002 | Douk et al. | 2003/0100919 A1 | 5/2003 | Hopkins et al. |
| 2002/0151928 A1 | 10/2002 | Leslie et al. | 2003/0105472 A1 | 6/2003 | McAlister |
| 2002/0156520 A1 | 10/2002 | Boylan et al. | 2003/0105484 A1 | 6/2003 | Boyle et al. |
| 2002/0161389 A1 | 10/2002 | Boyle et al. | 2003/0105486 A1 | 6/2003 | Murphy et al. |
| 2002/0161390 A1 | 10/2002 | Mouw | 2003/0109824 A1 | 6/2003 | Anderson et al. |
| 2002/0161391 A1 | 10/2002 | Murphy et al. | 2003/0109897 A1 | 6/2003 | Walak et al. |
| 2002/0161392 A1 | 10/2002 | Dubrul | 2003/0114879 A1 | 6/2003 | Euteneuer et al. |
| 2002/0161393 A1 | 10/2002 | Demond et al. | 2003/0114880 A1 | 6/2003 | Hansen et al. |
| 2002/0161394 A1 | 10/2002 | Macoviak et al. | 2003/0120303 A1 | 6/2003 | Boyle et al. |
| 2002/0161395 A1 | 10/2002 | Douk et al. | 2003/0120304 A1 | 6/2003 | Kaganov et al. |
| 2002/0161396 A1 | 10/2002 | Jang et al. | 2003/0125764 A1 | 7/2003 | Brady et al. |
| 2002/0165557 A1 | 11/2002 | McAlister | 2003/0125765 A1 | 7/2003 | Blackledge et al. |
| 2002/0165573 A1 | 11/2002 | Barbut | 2003/0130680 A1 | 7/2003 | Russell |
| 2002/0165576 A1 | 11/2002 | Boyle et al. | 2003/0130681 A1 | 7/2003 | Ungs |
| 2002/0169472 A1 | 11/2002 | Douk et al. | 2003/0130682 A1 | 7/2003 | Broome et al. |
| 2002/0169474 A1 | 11/2002 | Kusleika et al. | 2003/0130684 A1 | 7/2003 | Brady et al. |
| 2002/0173815 A1 | 11/2002 | Hogendijk et al. | 2003/0130685 A1 | 7/2003 | Daniel et al. |
| 2002/0173819 A1 | 11/2002 | Leeflang et al. | 2003/0130686 A1 | 7/2003 | Daniel et al. |
| 2002/0177872 A1 | 11/2002 | Papp et al. | 2003/0130687 A1 | 7/2003 | Daniel et al. |
| 2002/0183781 A1 | 12/2002 | Casey et al. | 2003/0130688 A1 | 7/2003 | Daniel et al. |
| 2002/0183782 A1 | 12/2002 | Tsugita et al. | 2003/0135232 A1 | 7/2003 | Douk et al. |
| 2002/0183783 A1 | 12/2002 | Shadduck | 2003/0135233 A1 | 7/2003 | Bates et al. |
| 2002/0188313 A1 | 12/2002 | Johnson et al. | 2003/0139764 A1 | 7/2003 | Levinson et al. |
| 2002/0188314 A1 | 12/2002 | Anderson et al. | 2003/0139765 A1 | 7/2003 | Patel et al. |
| 2002/0193824 A1 | 12/2002 | Boylan et al. | 2003/0144685 A1 | 7/2003 | Boyle et al. |
| 2002/0193825 A1 | 12/2002 | McGuckin et al. | 2003/0144686 A1 | 7/2003 | Martinez et al. |
| 2002/0193826 A1 | 12/2002 | McGuckin et al. | 2003/0144687 A1 | 7/2003 | Brady et al. |
| 2002/0193827 A1 | 12/2002 | McGuckin et al. | 2003/0144688 A1 | 7/2003 | Brady et al. |
| 2002/0193828 A1* | 12/2002 | Griffin et al. ................. 606/200 | 2003/0144689 A1 | 7/2003 | Brady et al. |
| 2002/0198561 A1 | 12/2002 | Amplatz | 2003/0150821 A1 | 8/2003 | Bates et al. |
| 2003/0004536 A1 | 1/2003 | Boylan et al. | 2003/0153935 A1 | 8/2003 | Mialhe |
| 2003/0004538 A1 | 1/2003 | Secrest et al. | 2003/0153942 A1 | 8/2003 | Wang et al. |
| 2003/0004539 A1 | 1/2003 | Linder et al. | 2003/0153943 A1 | 8/2003 | Michael et al. |
| 2003/0004540 A1 | 1/2003 | Linder et al. | 2003/0153944 A1 | 8/2003 | Phung et al. |
| 2003/0004541 A1 | 1/2003 | Linder et al. | 2003/0153945 A1 | 8/2003 | Patel et al. |
| 2003/0004542 A1 | 1/2003 | Wensel et al. | 2003/0158518 A1 | 8/2003 | Schonholz et al. |

| | | |
|---|---|---|
| 2003/0158574 A1 | 8/2003 | Esch et al. |
| 2003/0158575 A1 | 8/2003 | Boylan et al. |
| 2003/0163158 A1 | 8/2003 | White |
| 2003/0163159 A1 | 8/2003 | Patel et al. |
| 2003/0167068 A1 | 9/2003 | Amplatz |
| 2003/0167069 A1 | 9/2003 | Gonzales et al. |
| 2003/0171769 A1 | 9/2003 | Barbut |
| 2003/0171770 A1 | 9/2003 | Kusleika et al. |
| 2003/0171771 A1 | 9/2003 | Anderson et al. |
| 2003/0171772 A1 | 9/2003 | Amplatz |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176887 A1 | 9/2003 | Petersen |
| 2003/0176888 A1 | 9/2003 | O'Connell |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0717769 | 9/2003 | Barbut |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191492 A1 | 10/2003 | Gellman et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0199819 A1 | 10/2003 | Beck |
| 2003/0199917 A1 | 10/2003 | Knudson et al. |
| 2003/0199918 A1 | 10/2003 | Patel et al. |
| 2003/0199919 A1 | 10/2003 | Palmer et al. |
| 2003/0199920 A1 | 10/2003 | Boylan et al. |
| 2003/0199921 A1 | 10/2003 | Palmer et al. |
| 2003/0204168 A1 | 10/2003 | Bosma et al. |
| 2003/0204202 A1 | 10/2003 | Palmer et al. |
| 2003/0204203 A1 | 10/2003 | Khairkhahan et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0208253 A1 | 11/2003 | Beyer et al. |
| 2003/0212428 A1 | 11/2003 | Richter |
| 2003/0212429 A1 | 11/2003 | Keegan et al. |
| 2003/0212432 A1 | 11/2003 | Khairkhahan et al. |
| 2003/0212433 A1 | 11/2003 | Ambrisco et al. |
| 2003/0216774 A1 | 11/2003 | Larson |
| 2003/0220665 A1 | 11/2003 | Eskuri et al. |
| 2003/0220667 A1 | 11/2003 | Van der Burg et al. |
| 2003/0225435 A1 | 12/2003 | Hunter et al. |
| 2003/0229374 A1 | 12/2003 | Brady et al. |
| 2003/0233117 A1 | 12/2003 | Adams et al. |
| 2004/0006364 A1 | 1/2004 | Ladd |
| 2004/0006370 A1 | 1/2004 | Tsugita |
| 2004/0039412 A1 | 2/2004 | Isshiki et al. |
| 2004/0059372 A1 | 3/2004 | Tsugita |
| 2004/0064067 A1 | 4/2004 | Ward |
| 2004/0068271 A1 | 4/2004 | McAlister |
| 2004/0078044 A1 | 4/2004 | Kear |
| 2004/0082962 A1 | 4/2004 | Demarais et al. |
| 2004/0093016 A1 | 5/2004 | Root et al. |
| 2004/0098022 A1 | 5/2004 | Barone |
| 2004/0098033 A1 | 5/2004 | Leeflang et al. |
| 2004/0098112 A1 | 5/2004 | DiMatteo et al. |
| 2004/0106944 A1 | 6/2004 | Daniel et al. |
| 2004/0116831 A1 | 6/2004 | Vrba |
| 2004/0133232 A1 | 7/2004 | Rosenbluth et al. |
| 2004/0158278 A1 | 8/2004 | Becker et al. |
| 2004/0164030 A1 | 8/2004 | Lowe et al. |
| 2004/0167567 A1 | 8/2004 | Cano et al. |
| 2004/0176794 A1 | 9/2004 | Khosravi |
| 2004/0176833 A1 | 9/2004 | Pavcnik et al. |
| 2004/0236369 A1 | 11/2004 | Dubrul |
| 2005/0038468 A1 | 2/2005 | Panetta et al. |
| 2006/0100544 A1 | 5/2006 | Ayala et al. |
| 2006/0100545 A1 | 5/2006 | Ayala et al. |

FOREIGN PATENT DOCUMENTS

WO    WO 99/44510    9/1999

\* cited by examiner

EMBOLIC PROTECTION DEVICE WITH AN INTEGRAL BASKET AND BAG

RELATED APPLICATION

This application claims the benefit of U.S. Provisional Application No. 60/698,350, filed Jul. 12, 2005, the entire contents of which are incorporated herein by reference.

BACKGROUND

The present invention relates to medical devices. More particularly, the present invention relates to embolic protection devices and methods for capturing emboli within a body vessel.

The present invention relates to medical devices. More particularly, the present invention relates to embolic protection devices and methods for capturing emboli within a body vessel.

Presently, there are a number of treatments for embolic protection to prevent emboli and blood clots from traveling within the vasculature that create undesirable medical conditions, such as ischemic stroke, brain aneurysm, and pulmonary embolism. For example, vena cava filters are commonly employed to trap blood clots and emboli in the vena cava filter to prevent pulmonary embolism; snares and baskets (for example, stone retrieval baskets) are generally employed to retrieve urinary calculi; and occlusion coils are typically employed to occlude aneurysms and accumulate thrombi in a body vessel.

Treatments for stenotic lesions create a potential in releasing blood clots and other thrombi plaque in the vasculature of the patient, for example, in the treatment for carotid artery stenosis. Generally, carotid artery stenosis (also called carotid artery disease) is the narrowing of the carotid arteries, which are the main arteries in the neck that supply blood to the brain, usually caused by plaque build-up in the carotid artery, creating a relatively high risk factor for ischemic stroke. Plaque forms when cholesterol, fat and other substances form in the inner lining of an artery. This formation process is know as atherosclerosis.

Depending on the degree of stenosis and the patient's overall condition, carotid artery stenosis has been treated with surgery. This procedure, known as carotid endarterectomy, removes the plaque from the arterial walls. Carotid endarterectomy has been shown to benefit patients with arteries that are substantially narrowed, for example, by about 70% or more. For people with arteries that are not as narrowed, for example, less than about 50%, an anti-clotting drug, such as anti-platelet agents and anticoagulants, may be prescribed to reduce the risk of ischemic stroke.

Carotid angioplasty is a more recently developed treatment for carotid artery stenosis. This treatment uses balloons with or without stents to open a narrowed artery. This procedure can be performed through a standard percutaneous transfemoral approach with the patient anesthetized using light intravenous sedation. At the stenosis area, an angioplasty balloon is delivered to predilate the stenosis in preparation for placement of a stent. The balloon is then removed and exchanged through a catheter for a stent delivery device. Once in position, a stent is deployed across the stenotic area. If needed, another balloon can be placed inside the deployed stent for post-dilation to ensure that the struts of the stent are pressed firmly against the inner surface of the vessel wall.

During the stenosis procedure, there is a risk of blood clots and thrombi being undesirably released into the blood flow within the vasculature. Embolic or distal protection devices have been implemented to capture emboli. However, many current embolic protection devices restrict flow when deployed within the vasculature of the patient. Moreover, many embolic protection devices are relatively difficult to collapse and retrieve after the need for such a device in the vasculature passes.

In view of the above, it is apparent that there exists a need for an improved device and method for distally protecting and capturing emboli within a body lumen during a stenosis procedure.

SUMMARY

The present invention generally provides an embolic protection device that minimizes restricted flow when deployed within the vasculature of a patient and that is relatively easy to retrieve after the risk of releasing blood clots and thrombi within the vasculature has passed. The embolic protection device includes a basket defined by a section of a set of wires arranged as a plurality of struts. These struts are coupled together at their distal ends as well as to the distal end of a core wire or mandrel. Another section of the wires spirals around the core wire to define a hollow channel in which the core wire can reciprocate. Thus, pulling or pushing a proximal end of the core wire relative to the spiraled section expands or contracts the basket. A filter bag is attached to the basket for capturing emboli when the basket is in an expanded configuration.

Hence, the filter bag, basket, and deployment mechanism are all one integral unit with a small cross sectional profile when the device is in a collapsed configuration. Thus, during delivery of the device, the small profile enables crossing a lesion without inadvertently dislodging material from the lesion site.

Further features and advantages will be apparent from the following description, and from the claims.

DETAILED DESCRIPTION

Figure 1:
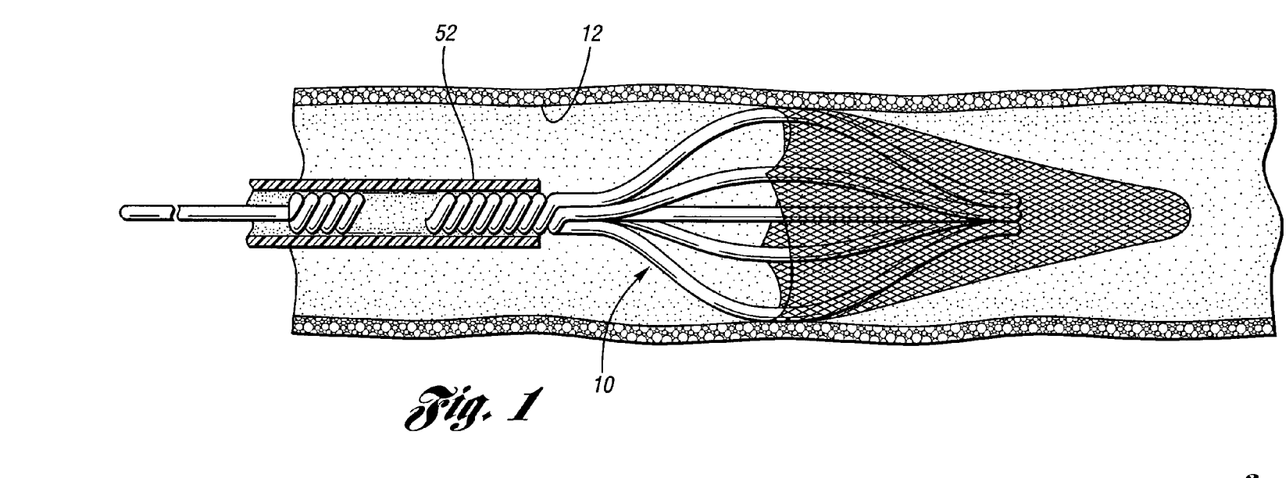
FIG. 1 is an environmental view of an embolic protection device in accordance with one embodiment of the present invention.
Figure 2:
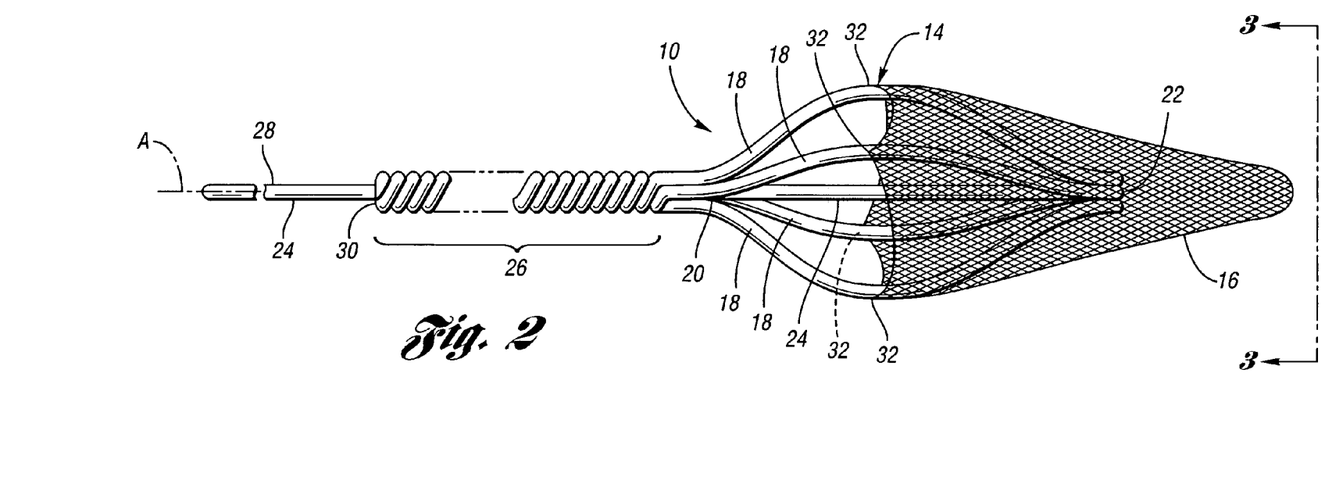
FIG. 2 is a perspective view of the embolic protection device of FIG. 1.

Referring now to FIG. 1, an embolic protection device embodying the principles of the present invention is illustrated therein and designated at 10. The device 10 captures emboli during treatment of a stenotic lesion in a body vessel 12 in accordance with an embodiment of the present invention. As shown in FIGS. 1 and 2, the device 10 includes a basket 14 and a filter portion or bag 16 attached to the basket 14 for capturing emboli in the body vessel 12. The basket 14 is defined by a section of a set of wires arranged as struts 18 that extend longitudinally from a proximal end 20 of the basket 14 to a distal end 22. A distal end of a core wire 24 is attached to the distal end 22 of the struts 18. Another section of the set of wires is twisted or spiraled to define a spiraled section 26 with a hollow channel through which the core wire 24 extends along a longitudinal axis A. A proximal end 28 of the core wire 24 extends beyond a proximal end 30 of the spiraled portion 26. The distal end of the core wire 24 is attached or coupled to the distal end 22 of the struts 18 by solder, or the distal ends may be embedded in a plastic material. The lip of the filter bag 16 is attached to the basket 14 only at attachments 32 of the struts 18 to define an opening into which clots or emboli flow when the filter is deployed in the vasculature. The attachments 32 may be glue or solder or any other biocompatible attachment mechanism. When in the expanded configuration, the struts 18 extend longitudinally and curve outwardly between the proximal end 20 of the basket 14 and the distal end 22. The attachments 32 are typically located on the struts 18 approximately where the basket achieves its maximum diameter when expanded so that blood flows through the filter bag 16 and not around it.

Figure 3:
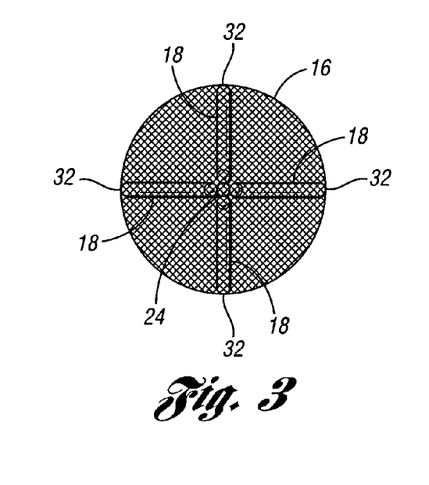
FIG. 3 is a end view of the embolic protection device of FIG. 1.

Since the core wire 24 is attached only at the distal end 22 of the basket 14 and is able to reciprocate within the hollow channel of the spiraled section 26, grasping the proximal end 28 of the core wire 24 and pulling it relative to the proximal end 30 of the spiraled section 26, buckles the section of the struts 18 to expand the basket 14, and hence the filter bag 16. Conversely, pushing the core wire 24 relative to the spiraled section 26 collapses the basket 14 and bag 16 for delivery or retrieval of the device 10. This feature allows a catheter to ride over the spiraled section 26 and the struts 18 for relatively easy collapse and retrieval of the device 10. As shown in FIGS. 2 and 3, four wires define the basket 14 and the spiraled section 26. However, depending on the application, as few as three or more than four struts may be employed.

Figure 4:
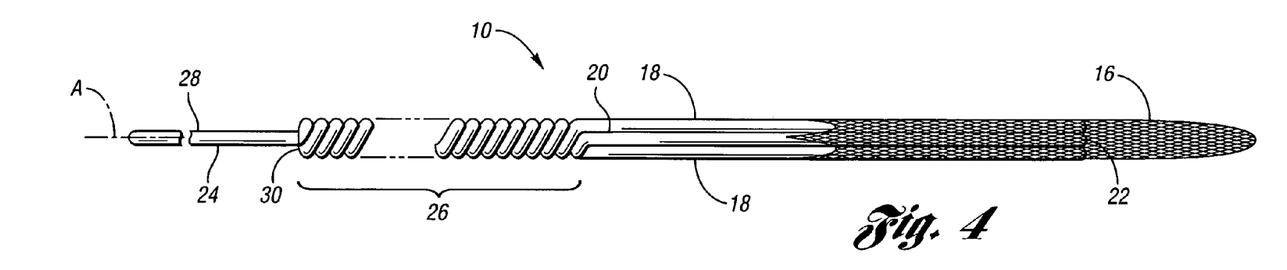
FIG. 4 is a side view of the embolic protection device in a collapsed configuration in accordance with one embodiment of the present invention.

FIG. 4 illustrates the device 10 in its collapsed or closed state in accordance with one embodiment of the present invention. As shown, the device 10 has a reduced diameter, occupying a cross-sectional profile less than the outer diameter of the device 10 in the expanded state. The struts 18 are generally straight and the bag 16 is collapsed about a portion of the struts 18. The portion of the bag 16 extending beyond the distal end 22 of the struts 18 may be folded back over the struts 18 for delivery of the device 10.

The struts 18 may be formed from any suitable material such as a superelastic material, stainless steel wire, cobalt-chromium-nickel-molybdenum-iron alloy, or cobalt-chrome alloy. It is understood that in some implementations the struts 18 may be formed of any other suitable material that will result in a self-opening or self-expanding basket 14, such as shape memory alloys. Shape memory alloys have the desirable property of becoming rigid, that is, returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that material returns to its remembered state. The transition temperature is dependent on the relative proportions of the alloying elements Ni and Ti and the optional inclusion of alloying additives.

In one embodiment, the struts 18 are made from Nitinol with a transition temperature that is slightly below normal body temperature of humans (that is, about 98.6° F.). Thus, when the basket 14 is deployed in a body vessel and exposed to normal body temperature, the alloy of the basket 14 will transform to austenite, that is, the remembered state, which for certain implementations is the expanded configuration when the basket 14 is deployed in the body vessel. To remove the basket 14, the basket 14 is cooled to transform the material to martensite, which is more ductile than austenite, making the basket 14 more malleable, and hence more easily collapsible by pushing the core wire 24 relative to the spiraled section 20 and then pulling the device 10 into a lumen of a catheter for removal.

In other embodiments, the basket 14 may be self-closing or self-collapsing. In such embodiments, the struts 18 may be made from Nitinol with a transition temperature that is above normal body temperature of humans. Thus, when the basket 14 is deployed in a body vessel and exposed to normal body temperature, the basket 14 is in the martensitic state so that the basket 14 is sufficiently ductile to bend or form the basket 14 into an expanded configuration. To remove the basket 14, it is heated, for example, with a saline solution, to transform the alloy to austenite so that the basket 14 becomes rigid and returns to a remembered state, that is, a collapsed configuration The filter bag 16 may be formed from any suitable material to be used for capturing emboli from the stenotic lesion during treatment thereof while allowing blood to flow through it. In one embodiment, the filter bag 16 is made of connective tissue material for capturing emboli. The connective tissue may include extracellular matrix (ECM), which is a complex structural entity surrounding and supporting cells that are found within mammalian tissues. More specifically, ECM includes structural proteins (for example, collagen and elastin), specialized protein (for example, fibrillin, fibronectin, and laminin), and proteoglycans, a protein core to which are attached long chains of repeating disaccharide units termed glycosaminoglycans.

The extracellular matrix can be made of small intestinal submucosa (SIS). As known, SIS is a resorbable, acellular, naturally occurring tissue matrix composed of ECM proteins and various growth factors. SIS is derived from the porcine jejunum and functions as a remodeling bioscaffold for tissue repair. SIS has characteristics of an ideal tissue engineered biomaterial and can act as a bioscaffold for remodeling of many body tissues including skin, body wall, musculoskeletal structure, urinary bladder, and also supports new blood vessel growth. In many aspects, SIS is used to induce site-specific remodeling of both organs and tissues depending on the site of implantation. In theory, host cells are stimulated to proliferate and differentiate into site-specific connective tissue structures, which have been shown to completely replace the SIS material in time.

In some implementations, SIS is used to temporarily adhere the filter bag 16 to the walls of a body vessel in which the device 10 is deployed. SIS has a natural adherence or wettability to body fluids and connective cells that form the connective tissue of a body vessel wall. Because of the temporary nature of the duration in which the device 10 is deployed in the body vessel, host cells of the wall will adhere to the filter bag 16 but will not differentiate, allowing for retrieval of the device 10 from the body vessel.

In other embodiments, the filter bag 16 may be made of a mesh/net cloth, nylon, polymeric material, Teflon, or woven mixtures thereof.

In use, the device 10 expands from the collapsed state to the expanded state, engaging the basket 14 with the body vessel. In turn, the filter portion 16 expands to capture emboli during treatment of the stenotic lesion. After the device 10 is no longer needed, it may be retrieved. In some embodiments, a catheter is deployed longitudinally about the basket 14 after it has been collapsed by pulling on the core wire 24 relative to the spiraled section 26.

The embolic protection device 10 may be used independently without any other delivery system or mechanism. Alternatively, the device 10 may be used, for example, with an embolic protection assembly 50 as depited in FIGS. 5a and 5b.

Figure 5A:
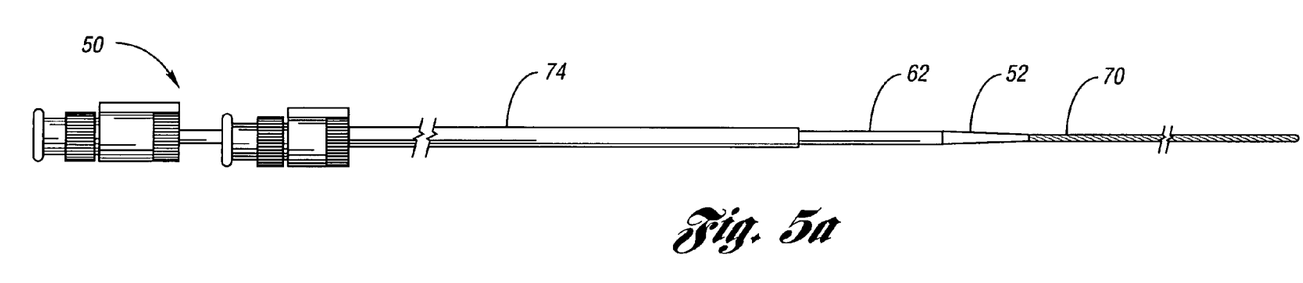
FIG. 5*a* is a side view of an embolic protection assembly for capturing emboli during treatment of a stenotic lesion in accordance with one embodiment of the present invention.
Figure 5B:
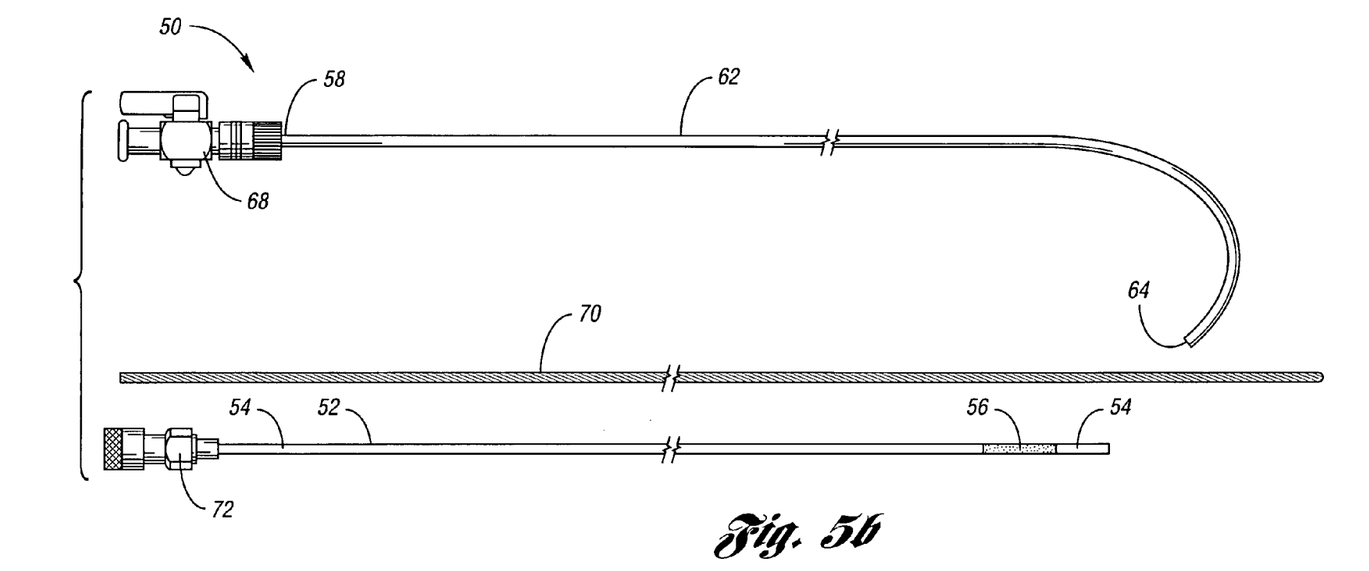
FIG. 5*b* is an exploded side view of the assembly in FIG. 5*a;*

As shown, the assembly 50 includes a balloon catheter 52 having a tubular body 54 and an expandable balloon 56 attached to and in fluid communication with the tubular body 54 for angioplasty at a stenotic lesion. The assembly 50 also includes the embolic protection device mentioned above. The tubular body 54 is preferably made of soft flexible material such as silicon or any other suitable material. The balloon catheter 52 may include an outer lumen that is in fluid communication with the balloon 56 for inflating and deflating the balloon 56 and an inner lumen formed within the outer lumen for percutaneous guidance through the body vessel with a wire a guide and for deploying the embolic protection device 10. In certain implementations, the balloon catheter 52 has a proximal fluid hub 72 in fluid communication with the balloon 56 by way of the outer lumen for fluid to be passed through the outer lumen for inflation and deflation of the balloon 56 during treatment of the stenotic lesion.

The assembly 50 further includes an inner catheter 62 with a distal end 64 through which the balloon catheter 52 is disposed for deployment in the body vessel. The inner catheter 62 is preferably made of a soft, flexible material such as silicon or any other suitable material. Generally, the inner catheter 62 also has a proximal end 58 and a plastic adaptor or hub 68 to receive the embolic protection device 10 and balloon catheter 52. The size of the inner catheter 62 is based on the size of the body vessel into which the catheter 62 is inserted, and the size of the balloon catheter 52.

The assembly 50 may also include a wire guide 70 configured to be percutaneously inserted within the vasculature to guide the inner catheter 62 to a location adjacent a stenotic lesion. Alternatively, the embolic protection device 10 may be employed as a wire guide.

To deploy the embolic protection device 10, the device 10 is placed in the inner lumen of the balloon catheter 52 prior to treatment of the stenotic lesion. The distal protection device is then guided through the inner lumen preferably from the hub 72 and distally beyond the balloon 56 of the balloon catheter 52, exiting from the distal end of the balloon catheter 52 to a location within the vasculature downstream of the stenotic lesion.

The assembly 50 may include a polytetrafluoroethylene (PTFE) introducer sheath 74 for percutaneously introducing the wire guide 70 and the inner catheter 62 in a body vessel. Of course, any other suitable material may be used. The introducer sheath 74 may have any suitable size, e.g., between about three-french to eight-french. The introducer serves to allow the inner and balloon catheters 62, 52 to be inserted percutaneously to a desired location in the body vessel. The introducer sheath 74 receives the inner catheter 62 and provides stability to the inner catheter at a desired location of the body vessel. For example, as the introducer sheath 74 is held stationary within a common visceral artery, it adds stability to the inner catheter 62, as the inner catheter 62 is advanced through the introducer sheath 74 to a dilatation area in the vasculature.

When the distal end 64 of the inner catheter 62 is at a location downstream of the dilatation area in the body vessel, the balloon catheter 52 is inserted through the inner catheter 62 to the dilatation area. The embolic protection device 10 is then loaded at the proximal end of the balloon catheter 52 and is advanced coaxially through the inner lumen of the balloon catheter 52 for deployment through the distal end of the balloon catheter. In this embodiment, the proximal end 28 of the core wire 24 can be used to mechanically advance or push the embolic protection device 10 through the catheter.

Figure 6:
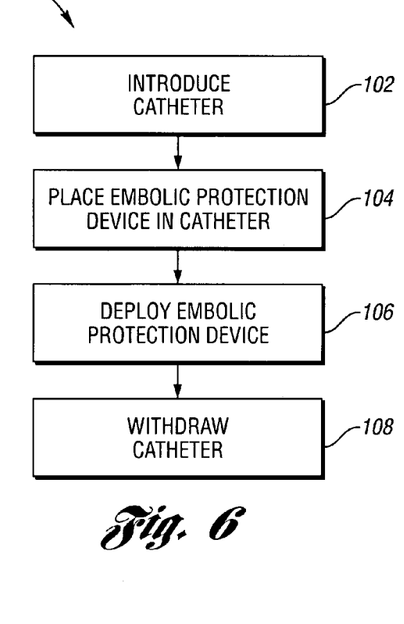
FIG. 6 is a flow chart of one method for embolic protection during treatment of a stenotic lesion in a body vessel.

FIG. 6 depicts a sequence of steps of a process 100 for embolic protection during treatment of stenotic lesion in a body vessel. The process 100 includes percutaneously introducing the balloon catheter 52 in a body vessel in a step 102, after the inner catheter 62 is disposed to a dilatation area within the body vessel. The physician may use any suitable means, for example, fluoroscopy, of verifying the placement of the balloon catheter at a dilatation area.

Next, in step 104, the embolic protection device 10 is placed in the collapsed state in the inner lumen of the balloon catheter 52 and advanced beyond the distal end of the balloon catheter, and, hence, beyond the dilatation area. The process 100 further includes deploying the device in an expanded state downstream from the stenotic lesion to capture emboli during treatment of the stenotic lesion in step 106. Optionally, the catheter may be withdrawn in step 108, and an alternative treatment device may be placed over the spiraled section 26 of the embolic protection device 10, that is, the device 10 may serve as a wire guide for the alternative treatment device.

Figure 7:
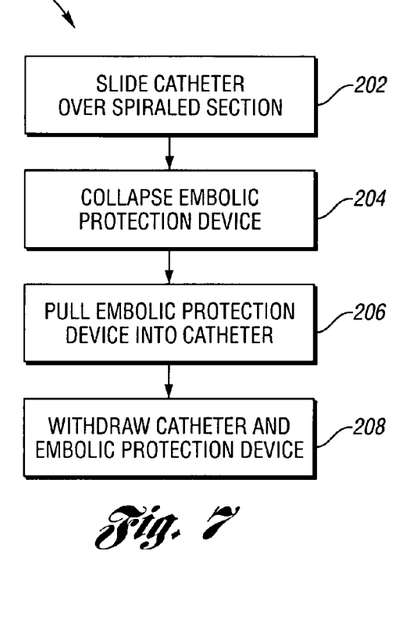
FIG. 7 is a flow chart of one method for retrieving an embolic protection device for post-treatment of a stenotic lesion in a body vessel.

In yet another example of the present invention, FIG. 7 depicts a process 200 for retrieving an embolic protection device for post-treatment of a stenotic lesion in a body vessel. In step 202, the process 200 includes sliding a catheter, such as the balloon catheter 52, over the spiraled section 26 of the embolic protection device 10 when the device is in a deployed state within the body vessel in step 202. Next, in step 204, the core wire 24 is pushed relative to the spiraled section 26 to collapse the basket 14, as well as the bag 16. The process 200 further includes, in step 206, retracting the embolic protection device 10 into the balloon catheter, and, in step 208, retrieving the catheter and the embolic protection device from the body vessel.

The above and other embodiments are within the scope of the following claims.

What is claimed is:

1. An embolic protection device for capturing emboli, the device comprising:

a set of wires, a section of which is arranged as struts defining a basket with a distal end and a proximal end, the basket having an expanded state and a collapsed state, the set of wires including a spiraled section that defines a hollow channel extending from the proximal end of the basket to a proximal end of the spiraled section;

a core wire with a distal end coupled to the distal end of the basket, the core wire extending from the distal end of the basket through the hollow channel to a proximal end of the core wire that extends beyond the proximal end of the spiraled section;

a filter bag with a lip attached to the struts only at attachments located on the struts generally where the basket achieves its maximum diameter when the basket is in the expanded state for capturing emboli, wherein movement of the core wire in the proximal direction relative to the spiraled section causes the basket, and hence the filter bag, to open to the expanded state, and wherein movement of the core wire in the distal direction relative to the spiraled section causes the basket, and hence to the filter bag, to close to the collapsed state; and a catheter including a tubular body defining an inner lumen configured to slide over the spiraled section and the struts for collapse and retrieval of the device.

2. The device of claim 1 wherein the number of struts is four.

3. The device of claim 1 wherein the opening of the filter bag faces toward the stenotic lesion.

4. The device of claim 1 wherein the filter bag is made of a mesh material.

5. The device of claim 1 wherein the filter bag is made of connective tissue including extracellular matrix.

6. The device of claim 5 wherein the extracellular matrix is made of small intestinal submucosa.

7. The device of claim 1 wherein the set of wires is made of shape memory material with a transition temperature.

8. The device of claim 1 wherein the set of wires is made of superelastic material.

9. The device of claim 8 wherein the superelastic material is Nitinol.

10. An embolic protection device for capturing emboli, the device comprising:
a basket with a set of struts extending from a distal end to a proximal end of the basket, the basket having an expanded state and a collapsed state;
spiraled wires that define a hollow channel extending from the proximal end of the basket to a proximal end of the spiraled wires;
a catheter including a tubular body defining an inner lumen configured to slide over the spiraled wires and the struts for collapse and retrieval of the device;
a core wire with a proximal end and a distal end coupled to the distal end of the basket, the core wire extending from the distal end of the basket through the hollow channel to the proximal end of the core wire, the proximal end of the core wire extending beyond the proximal end of the spiraled wires, the core wire movable within the inner lumen of the catheter; and
a filter bag with a lip attached to the struts only at attachments located on the struts generally where the basket achieves its maximum diameter when the basket is in the expanded state for capturing emboli,
movement of the core wire within the catheter in the proximal direction relative to the spiraled wires causing the basket, and hence the filter bag, to open to the expanded state, and movement of the core wire within the catheter in the distal direction relative to the spiraled wires causing the basket, and hence to the filter bag, to close to the collapsed state.

11. The device of claim 10 wherein the number of struts is four.

12. The device of claim 10 wherein the opening of the filter bag faces toward the stenotic lesion.

13. The device of claim 10 wherein the filter bag is made of a mesh material.

14. The device of claim 10 wherein the filter bag is made of connective tissue including extracellular matrix.

15. The device of claim 14 wherein the extracellular matrix is made of small intestinal submucosa.

16. The device of claim 10 wherein the struts are made of shape memory material with a transition temperature.

17. The device of claim 10 wherein the struts are made of superelastic material.

18. The device of claim 17 wherein the superelastic material is Nitinol.

* * * * *